United States Patent [19]

Green

[11] Patent Number: 5,733,786
[45] Date of Patent: Mar. 31, 1998

[54] MERCURY DETERMINATION

[75] Inventor: Gary L. Green, Fort Collins, Colo.

[73] Assignee: Hach Company, Loveland, Colo.

[21] Appl. No.: 757,019

[22] Filed: Nov. 26, 1996

[51] Int. Cl.$^6$ .................................................. G01N 33/20
[52] U.S. Cl. ........................... 436/81; 436/161; 436/164; 436/167; 436/177; 436/178; 436/181; 436/182; 422/55; 422/68.1; 422/80; 422/83; 95/134
[58] Field of Search ........................... 436/73, 81, 161, 436/164, 167, 174, 177, 178, 181, 182; 422/55, 68.1, 70, 80, 83; 95/116, 133, 134

[56] References Cited

U.S. PATENT DOCUMENTS

| | | | |
|---|---|---|---|
| 3,713,776 | 1/1973 | Capvano | 422/62 |
| 4,101,631 | 7/1978 | Ambrosini et al. | 423/210 |
| 4,125,376 | 11/1978 | Razulis | 436/79 |
| 4,814,152 | 3/1989 | Yan | 423/210 |
| 4,920,057 | 4/1990 | Castaneda | 436/77 |
| 5,202,301 | 4/1993 | McNamara | 502/417 |
| 5,300,137 | 4/1994 | Weyand et al. | 75/670 |
| 5,487,871 | 1/1996 | McDow et al. | 422/80 |

*Primary Examiner*—Maureen M. Wallenhorst
*Attorney, Agent, or Firm*—Dean P. Edmundson

[57] ABSTRACT

A method is described for quantitative determination of mercury present in a sample (liquid or solid). The method involves converting mercury compounds to elemental mercury, removing all elemental mercury from the sample in vapor form by means of vacuum, passing the mercury vapor through a column which absorbs and captures all of the mercury vapor by converting it to a halide compound, eluting the mercury halide from the column, and colorimetrically analyzing for the amount of mercury halide collected.

20 Claims, 2 Drawing Sheets

MERCURY DETERMINATION

FIELD OF THE INVENTION

This invention relates to methods and techniques for quantitative determination of mercury. More particularly, this invention relates to a cold vapor mercury determination for detecting very low levels of mercury (e.g., in water samples).

BACKGROUND OF THE INVENTION

Mercury occurs in the environment due to natural degassing of the earth's crust and also because of various industrial activities. Mercury is used in a variety of products. Accordingly, mercury finds its way into water and other areas of the environment from a variety of sources.

Mercury is a very toxic element. Consequently, it is very important to monitor its presence in water and foods.

When mercury is found at significant concentrations in the environment, it is usually the result of man-made pollution. This pollution is the result of industrial activity. Once in the environment, mercury will bioaccumulate in most forms of life. This accumulation in the food chain eventually reaches humans. Bioaccumulation of dimethylmercury in fish has caused several fatalities as in Minimata Japan between 1953 to 1968. Hence, there is a need to monitor for mercury in environmental samples and at sources of industrial discharge.

The duty of monitoring for mercury pollution is taken on by a wide variety of people. In industry, environmental compliance managers send samples of industrial waste water to contract laboratories for testing. Drinking water utilities are required monitor for mercury contamination on a regular basis. In addition, there are several environmental watchdog agencies which take samples from lakes, streams, soils and the like. Most of the testing is completed by contract laboratories. These laboratories have expensive, sophisticated equipment and highly-skilled operators to do the analysis following established methodology.

It is because of the difficulty associated with current technology that most samples have to be sent to contract laboratories for analysis. Common mercury analysis is performed by the flameless atomic absorption technique. In this technique a sample is first treated by digestion to convert compounds to the mercuric ion. Mercuric ions are reduced to elemental mercury in a special vessel, then purged from the solution in a closed system. Mercury vapor passes through a cell positioned in the light path of an atomic absorption spectrophotometer. The mercury vapor absorbs radiation at 253.7 nm. Absorbance or peak height is measured as function of mercury concentration.

There is a need to put a method for trace mercury determination in the hands of the general public. However, the flameless atomic absorption technique has several interference and difficulties which mandate operation by skilled personnel. First, care must be taken to purge chlorine from the vessel before reduction of mercuric ions. Chlorine may be produced in the digestion procedure and will absorb at 253 nm. Interference from certain volatile organic materials which absorb at this wavelength is also possible. Second, special drying tubes are required to remove vapor from the purging air stream prior to reaching the cell. Third, the air flow rate has to be extremely reproducible from calibration to sample analysis. Changes in temperature and barometric pressure and plugging of the drying tube can cause variation in the purging air flow rate. Often the calibration procedure has to be run several times during a day to maintain accuracy. Finally, the system has to be optimized to produce a plug of mercury vapor from the sample a rapidly as possible. If mercury vapor is not removed from the sample very quickly then the plug size is reduced. This lessens sensitivity in the determination.

The concentration of mercury vapor to lower sensitivity of the flameless technique has been employed. However, the approach used to capture mercury vapor involves preconcentration as an amalgam. The amalgam is usually formed with gold foil or gold coated onto a sand trap. Mercury vapor is then desorbed thermally and again measured by the absorption of ultraviolet radiation. Mercury cannot be removed the amalgam by simple elution. While the amalgamation step eliminates some of the interferences in the common flameless procedure described above it still has its drawbacks. The instrumentation is even more expensive than common dedicated analyzers. Also, the thermal desorption step must be extremely reproducible for accuracy.

There has not heretofore been provided a technique or method for quantitative determination of mercury having the features and advantages provided by the present invention.

SUMMARY OF THE PRESENT INVENTION

In accordance with the present invention there is provided an easy-to-use and effective method for the quantitative determination of mercury (even at trace amounts).
The method involves (a) digesting the sample at elevated temperature to convert all mercury which is present to the +2 ion;

(b) converting all mercury ion to elemental mercury;

(c) removing all elemental mercury from the sample in vapor form by means of vacuum;

(d) passing the mercury vapor through a column which is adapted to absorb and capture all of the mercury vapor by converting it to a halide compound;

(e) eluting the mercury halide from the column; and (f) colorimetrically analyzing for the amount of mercury collected.

The method of this invention is applicable to the determination of mercury in both solid and liquid samples, regardless of the form in which mercury may be present in the sample (i.e., elemental, inorganic or organic compounds). Organic mercury compounds may be covalently bound or strongly complexed mercury compounds. The method can be used for determination of mercury in drinking, surface, saline, domestic and industrial waste waters. In addition, the method can be used for mercury determination in soils, sediments, sludge, fish tissue, etc.

The method of this invention is very accurate for determining the amount of mercury present in a sample. The method can be performed by unskilled personnel, and the method does not suffer from the interferences and difficulties associated with the atomic absorption technique. Chlorine and volatile organic vapors do not present a problem, and removal of water vapor is not required.

Variation in the flow rate of the air drawn through the sample to remove mercury vapor does not limit reproducibility or sensitivity of the method. The air flow need only be sufficient in volume and duration for complete removal of mercury from the sample. Mercury vapor may come out of the sample in the first minute of purging or the last. The plug size is irrelevant because mercury vapor is absorbed and preconcentrated by a chemical reaction on an absorber column.

Although preconcentrating mercury vapor as a gold amalgam has a sensitivity greater than the present method, the amalgamation technique still requires reagent preparation and calibration by a skilled operator. The present method makes use of ready-to-use reagents and precalibrated instrumentation. Therefore, the method of this invention is useful in a wide variety of markets where the atomic absorption method is too costly or cumbersome.

The method of this invention employs a novel combination of physical and analytical chemistry. This method can be used by environmental compliance managers in industry or anyone interested in monitoring for mercury pollution in a variety of sample types.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
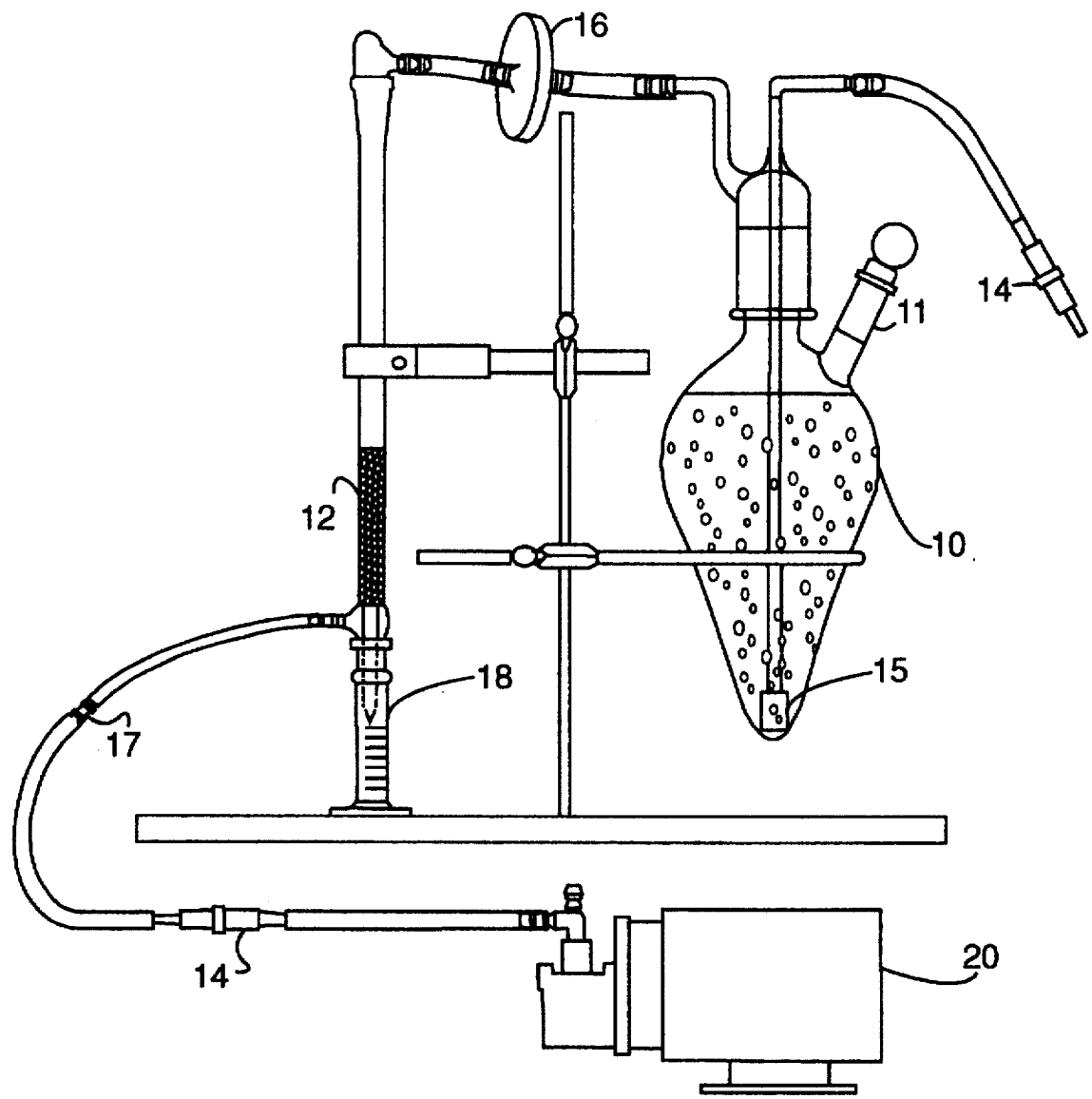
FIG. 1 is an elevational view of a preferred embodiment of apparatus used in the practice of this invention.

The method of this invention is applicable to the determination of mercury in drinking, surface, saline, domestic and industrial waste waters. In addition, this method is applicable to determination of mercury in soils, sediments, sludge, fish tissue, etc.

Forms of mercury which may be present in the sample may be elemental, inorganic and organic mercurials. Organic mercurials may be covalently bound or strongly complexed mercury compounds.

The linear range of the colorimetric method involves 0.1 µg $Hg^{2+}$ to 3.0 µg $Hg^{2+}$. The method uses one liter of aqueous sample to achieve a range of 0.1 µg/L Hg to 3.0 µg/L Hg. The range of the method for solid samples is from 100 µg Hg/Kg to 12 mg Hg/Kg using a sample size of 1 gram and 0.25 gram, respectively The range of the method may be extended to higher levels by selection of a smaller sample size. The mercury present in a sample is less than about 3 parts per billion by weight.

The sample to be analyzed is collected in a manner to eliminate combination during the sampling process that would compromise trace mercury determination. 10 mL of 12N hydrochloric acid is added to a rigorously cleaned glass, fluoropolymer or polyethylene terephthalate (PET) container to preserve an aqueous sample. One liter of sample is collected in the container. The container should be filled completely full to minimize air space when closed. Close a glass container with a ground glass stopper. Close a fluoropolymer bottle with a fluoropolymer or fluoropolymer-lined cap. Close a PET container with a PET cap or a polypropylene cap (no liner).

Solid samples must be protected from the loss of volatile mercury compounds after sampling. The sample may be analyzed without drying followed by the determination of the moisture content in portion of sample. However, it is more convenient to analyze a dry sample. The sample must be dried at as low a temperature as possible because of the volatility of many mercury compounds. The recommended drying temperature is 40° C. After drying the sample should be passed through a sieve with 2 mm openings. Only the fraction passing through the sieve is mixed thoroughly and used.

Acid preserved aqueous samples are stable for a minimum of 6 months. Aqueous and solid samples should be stored at 4° C. ± 2° C. Direct reduction of many inorganic and organic mercurials to elemental mercury is difficult. These compounds must first be broken down to mercuric ions by digestion.

Aqueous samples are strongly acidified with concentrated sulfuric and nitric acids. Potassium permanganate and potassium persulfate are then added to the sample. The sample is heated to 90° C. for two hours. Some samples such as sea waters, industrial effluents or others high in organic matter or chloride concentration require additional permanganate. A deep purple color must persist throughout the two hour digestion. The sample is cooled to room temperature. A black precipitate manganese dioxide may settle out during cooling. If the digested sample does not have a purple color then the digestion may be incomplete, and more potassium permanganate is added. The sample is digested until a purple color persists.

A representative specimen of a solid sample that has been dried, sieved and thoroughly mixed is accurately weighed. The digestion of solid samples is carried out in a large, round bottom flask 0.25 to 1.00 gram of solid sample is added (containing 1 to 3.0 µg Hg). The flask is heated using an electric heater/stirrer. The flask is connected to a water cooled condenser to minimize loss of volatile mercury compounds. The digestion is carried out using a 1:1 mixture of concentrated sulfuric and nitric acids with potassium permanganate. The solution is heated to boiling for two hours. In samples containing high levels of organic matter an antifoaming agent (e.g., Antifoam B Silicon Emulsion from J. T. Baker or equivalent) is added. At the end of two hours 50% hydrogen peroxide is added through a capillary funnel. The solution is boiled several minutes to destroy excess peroxide. After cooling to room temperature, the digested solid sample is diluted with a dilute hydrochloric acid solution to prevent loss of mercury to the flask.

After the digestion, the sample is prereduced with hydroxylamine hydrochloride to destroy remaining oxidizing agents. Hydroxylamine hydrochloride is added until the purple color of potassium permanganate is destroyed. Manganese dioxide may form during the digestion procedure. Manganese dioxide is insoluble and may contain considerable occluded mercury. Enough hydroxylamine hydrochloride is added to dissolve any manganese dioxide which has formed.

The digested sample is then transferred into a specially shaped, glass, gas washing bottle 10. See FIG. 1. The shape of the gas washing bottle is designed to produce powerful mixing during the purging operation. Suspended and undissolved solids do not have to be filtered from solution. The bottle has a volume of 1,200 mL.

The mercury absorber column 12 is activated using two reagents. The reagents produce excess hypochlorous acid and hypochlorite ions in the glass bead packing of the absorber column. The absorber column is connected to the gas washing bottle after activation.

A sealed glass ampule of stannous sulfate solution is shaken to suspend undissolved reagent. The ampule is opened and the contents are added to the digested sample solution in the gas washing bottle through the side neck 11. The side neck of the gas washing bottle is stoppered. Stannous sulfate reduces mercuric ions in the solution to vaporizable elemental mercury.

A flow of ambient air through the apparatus is produced by applying vacuum to the downstream end by means of vacuum pump 20. First, ambient air passes through a sorbent tube 14 containing Hopcalite. Hopcalite removes possible mercury contamination from the entering air stream which would cause falsely high results. Next, the purified air flows into the gas washing bottle through a fritted glass, gas dispersion tube 15. The gas dispersion tube produces small air bubbles which purge he digested sample solution in the gas washing bottle. The solution is vigorously mixed by the bubbling air flow.

Elemental mercury partitions into the air bubbles flowing through the solution. The air stream physically separates elemental mercury from the solution. All elemental mercury is swept out within five minutes at the ideal air flow rate. The ideal air rate is 2.5 liters/minute. The flow may fall between 1 to 5 liters/minute without detrimental affect. Additional pruging time should be allowed at slower air flow rates.

The air stream containing mercury vapor from the gas washing bottle may contain an aerosol spray. The aerosol spray can carry contaminants from the digested sample into the absorber column. Therefore, the air stream passes through white C-Flex tubing to a filter 16. The filter contains a hydrophobic fluoropolymer membrane having a 0.45 µm pore size. The media is installed in a polypropylene housing. The aerosol spray is removed from the air stream by the fluoropolymer membrane. The air stream containing mercury vapor then passes through white C-Flex tubing to the mercury absorber column 12.

Excess activating solution in the mercury absorber column flows into a distilling receiver 18 when the initial air flow begins. The surface of the glass bead packing in the absorber column remains wet with activating solution during the purging operation. Mercury vapor in the air stream is oxidized to mercuric chloride when it comes into contact with the activating solution on the surface of the glass bead packing. The capacity of the mercury absorber column is greater than 7 µg Hg. The mercuric chloride formed in the absorber column is retained on the surface of the glass beads for the remainder of the purging operation.

The air stream, devoid of mercury vapor, then passes through another Hopcalite sorbent tube and exits into the atmosphere through the vacuum pump. The downstream Hopcalite sorbent tube is a safety device to protect the operator from mercury vapor. The sorbent tube captures mercury vapor in the event the mercury absorber column has not been properly activated or the capacity of the absorber column has been exceeded.

Mercuric chloride retained within the mercury absorber column is eluted into a distilling receiver 18 using a vacuum induced flow of a dilute acid solution. The concentration of mercury in original aqueous sample is selectively increased by a factor of 100 through the use of the mercury absorber column.

Analysis of the eluate in the distilling receiver is carried out directly. A sensitive colorimetric chemistry with ready-to-use reagents and precalibrated instrumentation is used for the mercury determination.

The shape of the gas washing bottle is that of an inverted pear. This shape causes powerful mixing of the contents during the purging operation without the use of other mixing devices such as magnetic stirring equipment. The gas washing bottle has two glass tubes sealed into the top. One tube reaches to the bottom of the bottle. At the bottom end of this tube is a fritted glass gas dispersion tube. The gas dispersion tube breaks up the entering air stream into small bubbles. The rising air bubbles produce the mixing action and purge mercury vapor from the solution in the gas washing bottle. The other tube sealed into the top allows for the outlet of air stream containing mercury vapor.

The mercury absorber column body is made from a vacuum adapter plus a distilling column. First, there is the inner delivery tube. The inner delivery tube is sealed inside one end of the hollow distilling column. The delivery tube reaches into the distilling receiver during operation. Also, the deliver tube supports a Pyrex glass wool plug on the bottom of the packing. Second, there is the vacuum adapter. The vacuum adapter allows the connection of a vacuum source using tubing. The vacuum adapter is designed such that the liquid flowing out of the packed column passes into the distilling receiver or erlenmeyer flask and does not flow into the tubing leading to the vacuum source.

Third, there are the ground glass joints at the top and bottom. The top joint holds a glass elbow which is connected to the fluoropolymer filter by tubing. The bottom joint connects to either a distilling receiver or an erlenmeyer flask, depending on the phase of the procedure.

Lastly, the most critical components of the mercury absorber column is the packed zone of glass beads. Glass beads are packed into the lower part of the hollow distilling column. The glass beads are held in place using Pyrex glass wool plugs. The beads are 50 to 70 mesh size. The size of the beads and the depth of packing determines the column's capacity and the air flow rate through the column. Smaller beads and longer packed zones favor greater capacity while reducing the air flow rate. As the air flow rate is lowered it takes longer to completely purge mercury vapor from the solution in the gas washing bottle. The optimized column uses 11 grams of glass beads to produce a zone 80 mm long. This allows maximum air flow through the column while providing a capacity over twice the upper limit of the colorimetric chemistry. The column must be taken through a rigorous decontamination procedure after packing. The glass beads, glass wool and distilling column glass all contain lead. The activating solution used in the procedure will dissolve lead from the surface of the glass. Lead in the eluant is a contaminant which will produce falsely high results in a mercury determination. The column is decontaminated using heated aqua regia and then concentrated hydrochloric acid. Once cleaned up, the decontamination procedure does not need to be repeated.

The distilling receiver 18 is similar to a mixing graduated cylinder. The distilling receiver has the correct female, standard taper joint to allow connection to the mercury absorber column. It is graduated in 0.2 mL divisions up to 10 mL. There is enough head space when stoppered to allow mixing which dissolves the colorimetric reagents.

The quick disconnect 17 in the tubing allows the temporary disruption of vacuum during the procedure without turning the vacuum pump on and off. The air stream flowing through the apparatus stops when the quick disconnect is separated.

Each mercury sorbent tube 14 comprises a housing containing replaceable mercury sorbent tube is used two places in the apparatus. The sorbent tube is manufactured by SKC and contains 0.5 grams of Hopcalite. Hopcalite is packed between glass wool in a glass tube 8 mm×110 mm. The glass ends are flame sealed after packing. Before use, the tube ends are opened using a breaker/capper tool available from Hach Company. The opened tube is placed into a housing which seals around the tube and protects it from breakage. All air flowing through the apparatus passes through the sorbent tubes. The tubes must be replaced at least with each new reagent set of 25 tests.

Any vacuum pump is acceptable so long as it produces an air flow within the recommended range of 1 to 5 liters per minute. The required vacuum force is small. The pump must produce a force only great enough to overcome the small pressure drop through the system.

The method of the present invention involves first converting all mercury ion in a selected sample to be tested to elemental mercury.

The particles used for the packed zone in the mercury absorber column may be any inert, noncontaminating material such as titania. The particles must not react with the activating reagents. The particles must not add a contaminant into the finish chemistry.

The support particles may be porous such as silica gel. However, porous particles require a larger volume of reagent for complete elution of captured mercuric chloride. The larger volume of eluant reduces the sensitivity of the method.

The size of support particles and the depth of packing determines the column's capacity and the air flow rate through the column. Smaller particles and longer packed zones favor greater capacity while reducing the air flow rate. As the air flow rate is lowered it takes longer to completely purge mercury vapor from the solution in the gas washing bottle.

Other reagents, besides hypochlorous acid and hypochlorite ions, may be used to activate the mercury absorber column. Hypobromous acid and hypobromite ions may be substituted. The application of these reagents uses the same apparatus and procedure as described above.

Also, bromine may be used to activate the mercury absorber column. Bromine is a liquid with a high vapor pressure. The apparatus would have to be modified to allow a stream of bromine vapor to flow through the mercury absorber column during the entire purging operation. One approach would involve placing a vial of liquid bromine in-line between the fluoropolymer filter and directly in front of the absorber column. The vial would have an air bleed valve and be plumbed in-line using a t-fitting. The purging air stream from the gas washing bottle would combine with a steady stream of bromine vapor from the vial. The combined streams would then pass into the absorber column. Mercury vapor would react with bromine vapor and produce mercuric bromide. Mercuric bromide is retained then eluted from the absorber column. Mercuric bromide can be determined directly with a colorimetric chemistry.

Iodine may also be used. Iodine is a solid and should be ground into small crystals. A short zone of iodine crystals is packed between glass wool plugs in a glass eyedropper tube. The packed tube of iodine completely replaces the mercury absorber column described above. A large charcoal filter must be used to protect the vacuum pump from iodine vapor formed during the purging operation. Mercury vapor will react on the surface of the iodine to form mercuric iodide. A weak solution of potassium iodide is used to scour the surface of the iodine crystals and elute mercuric iodide. Mercuric iodide can be determined directly with a colorimetric chemistry.

The sensitivity of the colorimetric determination will follow the order: $HgCl_2 > HgBr_2 > HgI_2$.

Any colorimetric indicator system which reacts with mercury may be used. Sample considerations involving interferences, pH, hardness and the like do not apply since mercury is physically removed from the sample.

Examples of other indicators include, but are not limited to, sulfonated dithizone, other porphine derivatives, rodamine 6G, 1,10-phenthroline, rose bengal and antipyrine basic dyes. The above scheme of separation and preconcentration of mercury allows for very sensitive indicators with low selectivity to be used. Optimum pH and wavelength absorption when using these other indicators should be individually determined.

The invention is further illustrated by means of the following examples.

EXAMPLE 1

In a fume hood, a liquid sample (1 liter) to be tested is added to a 2000 mL Erlenmeyer flask, after which a 50 mm magnetic stir bar is added. The sample is then stirred with the stir bar on a hot plate while adding 50 mL concentrated sulfuric acid and 25 mL concentrated nitric acid. Then there are added 4.0 grams potassium persulfate and 7.5 grams potassium permanganate.

The flask is covered with a watch glass, and the sample is heated to 90° C. after the reagents have dissolved. Boiling is avoided. The heating is continued at 90° with stirring for two hours. For a mercury standard or reagent blank in distilled water this heat step is not required. Some samples (e.g., sea water, industrial effluents or others high in organic matter or chloride) require additional permanganate. A deep purple color must persist throughout the two-hour digestion.

The digested sample is cooled to room temperature. A black precipitate of manganese dioxide may settle out during cooling. If the digested sample does not have a purple color then the digestion may be incomplete, and more potassium permanganate is added. Return the sample to the magnetic stirring hot plate and continue digestion until a purple color persists.

The cool, digested sample is returned to the cool, magnetic stirring hot plate and hydroxylamine-hydrochloride is added to the stirring, digested sample using a 0.5 gram measuring spoon. Wait at least 30 seconds between each reagent addition since the reduction of excess permanganate or manganese dioxide by hydroxylamine-hydrochloride is a slow reaction. Add the hydroxylamine-hydrochloride until the purple color of excess permanganate is destroyed. Continue adding hydroxylamine-hydrochloride until any manganese dioxide formed during the digestion procedure is dissolved. The stir bar is removed.

The digested sample is transferred to the Cold Vapor Gas Washing Bottle shown in FIG. 1. Suspended and undissolved solids do not have to be filtered from solution. The gas washing bottle is set in the supporting ring, and the top is placed on the gas washing bottle. The 100 mL Erlenmeyer flask is connected to the mercury absorber column.

Pipet 8 mL of a reagent (comprising sulfuric acid, 0.0028 L, and deionized water to make 1.0 liter) into the mercury absorber column. Connect the power to the vacuum pump and apply a vacuum to the mercury absorber column. Draw the excess reagent into the 100 mL Erlenmeyer flask. Disconnect the vacuum using the quick disconnect when the reagent begins to drip from the tip of the inner delivery tube on the mercury absorber column (about 10 seconds after start of vacuum). Do not draw enough air through the absorber column to begin drying the packing. The 100 mL Erlenmeyer flask is removed from the mercury absorber column and replaced with the 10 mL distilling receiver. Pipet 2 mL of 5.25% sodium hypochlorite solution into the mercury absorber column, and connect the mercury absorber column to the gas washing bottle using the glass elbow. Shake an ampule of a stannous sulfate solution (sulfuric acid, 0.014 L, stannous sulfate, 0.100 Kg, and deoxygenated, deionized water to make 1.00 liter) to suspend any undissolved solids. Open the ampule and shake the contents into the gas washing bottle using the side neck. Stopper the side neck on the gas washing bottle. Then, reconnect the vacuum to the mercury absorber column using the quick disconnect. The vacuum will pull sodium hypochlorite solution through the mercury absorber column packing then into the 10 mL distilling receiver. Air bubbles should be produced at the gas dispersion tube in the gas washing bottle. Start timing 5 minutes to purge elemental mercury from the sample. Acceptable air flow rate through the gas washing bottle is between 1.0 to 5.0 liters/minute. The nominal air flow rate through the gas washing bottle is 2.5 liters/minute. Additional purging time should be allowed for lower air flow rates. For example, if the air flow rate is 1.0 liter/minute then the purge time should be increased to 10 minutes. At the end of the 5 minutes disconnect the gas washing bottle from the mercury absorber column by removing the glass elbow from the top of the mercury absorber column. Continue operation of the vacuum pump. Pipet 8 mL of the sulfuric acid reagent into the mercury absorber column to elute the captured mercury. Continue applying a vacuum to pull the reagent through the mercury absorber column packing then into the distilling receiver. Disconnect the power from the vacuum pump when the volume in the distilling receiver reaches 10 mL. Remove the distilling receiver from the mercury absorber column and connect the 100 mL Erlenmeyer flask. Pipet 4 mL of the sulfuric acid reagent into the absorber column without applying a vacuum. This will keep the mercury absorber packing wet between use. The mercury absorber column eluate in the distilling receiver is now ready for analysis.

EXAMPLE 2

The eluate collected in Example 1 is now used in a colorimetric mercury determination procedure. An alkaline reagent (0.5 g, comprising equal weights of sodium nitrite and anhydrous sodium carbonate) is added to the eluate in the distilling receiver. This reagent destroys the excess hypochlorous acid and hypochlorite ions in the eluate and produces an alkaline pH. The nitrite is oxidized to nitrate by hypochlorous acid and hypochlorite ions. Nitrite is not a strong enough reducing agent to reduce mercury to the elemental form under the conditions and matrix of the test solution.

Then an indicator (0.22 g) is added to the solution in the distilling receiver. The indicator comprises:

| sodium chloride | 0.92323 Kg |
|---|---|
| Porphine, Tetra[4-(trimethyl-ammonio phenyl] derivative, tetra-tosylate salt | 0.140 g |
| potassium iodide | 0.07663 Kg |

This indicator contains a sensitive colorimetric indicator for mercury plus some potassium iodide. The indicator is a porphine derivative coated on sodium chloride as a support.

Then 8 drops of a sodium hydroxide solution (50% by weight) is added to the solution in the distilling receiver to raise the pH above 13. The receiver is closed with a stopper and then inverted to mix, after which the solution is transferred to a spectrophotometer sample cell. A reaction period of 2 minutes is timed.

The spectrophotometer is set to a wavelength of 412 nm, and the spectrophotometer is zeroed using the solution in the sample cell after the 2 minute reaction period.

Then a complexing reagent (0.3 g) is added to the sample cell. This reagent preferably comprises:

| L-cysteine (97%) | 0.6875 Kg |
|---|---|
| Sodium chloride | 0.3125 Kg |

The L-cysteine is a much stronger ligand for mercury than the indicator and therefore it breaks the mercury:porphine complex with the conversion of the released porphine to the free base form. This generates an absorbance increase at 412 nm. The absorbance increase is directly related to the concentration of mercury in the original sample. However, a mercury-free solution will produce a positive absorbance change with the addition of L-cysteine alone. This absorbance increase arises from a pH change in the solution. Sodium chloride is formulated into the reagent at a proportion which suppresses the positive absorbance change of a mercury-free solution. Thus, this formulation allows the measurement of the more sensitive positive absorbance change at 412 nm instead of the less sensitive absorbance decrease at 447 nm. In addition, a blank solution does not have an absorbance change.

Figure 2:
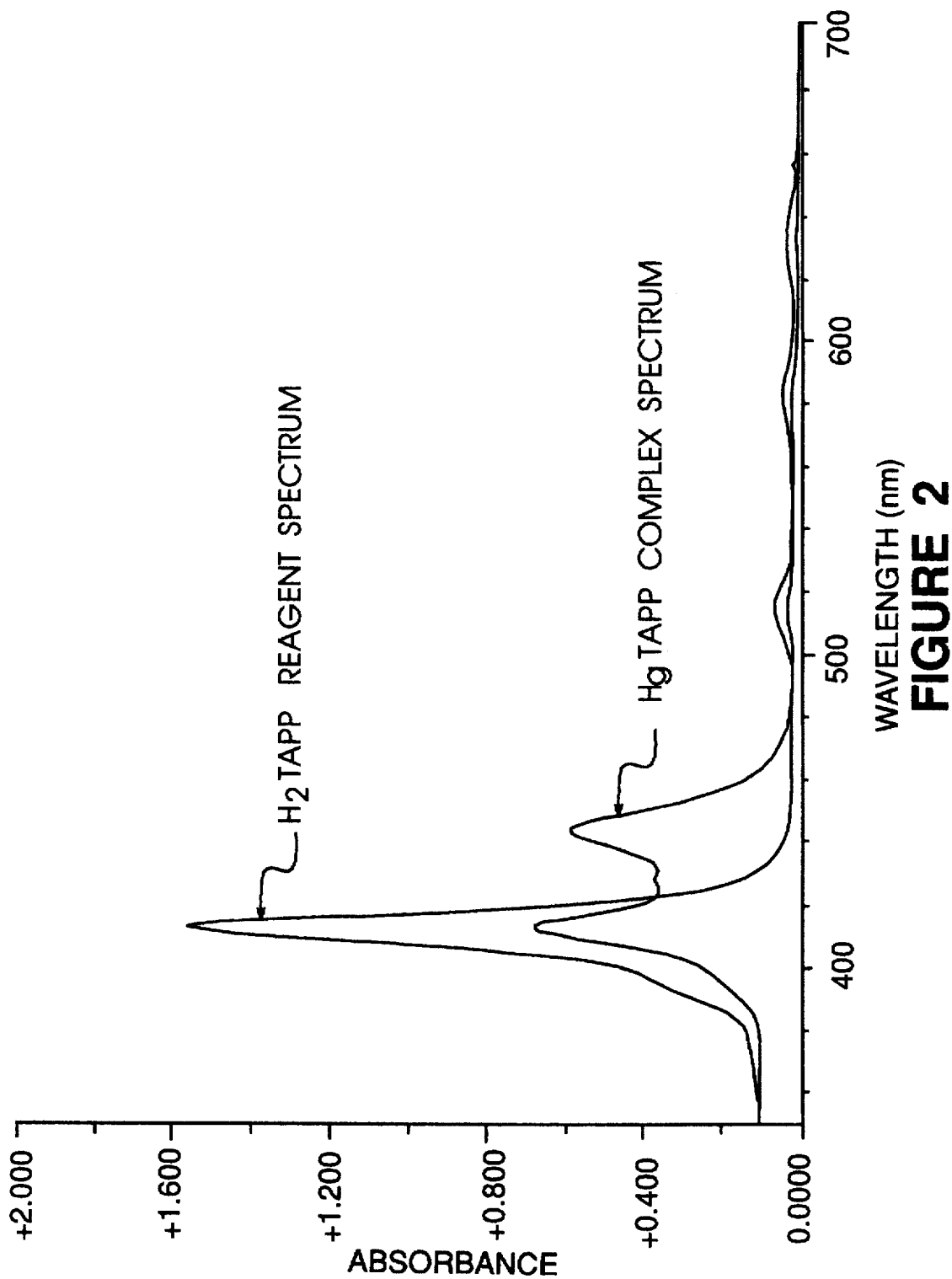
FIG. 2 is a graph illustrating absorption spectra of indicator and complexed mercury.

In other words, the mercury:porphine complex has an absorbance maximum at 447 nm with an extinction coefficient of $2.15 \times 10^5$ L $n^{-1}cm_{-1}$. Typical colorimetric analysis would use 447 nm as the analytical wavelength for absorbance measurements. However, the molar extinction coefficient of the mercury:porphine complex is less than that of the free base porphine ($3.62 \times 10^5$). Thus, when the complex is broken with the generation of free base porphine, then monitoring the absorbance change at 412 nm provides greater sensitivity. This is illustrated in FIG. 2. $H_2TAPP$ refers to tetra(p-trimethylammoniumphenyl)porphine, and HgTAPP complex refers to the mercury:porphine complex.

Other reagents which may be used to dissociate the mercury complex include, for example, sodium thiosulfate, sodium thioglycolate, and thiourea.

EXAMPLE 3

To demonstrate that the method of this invention is not affected by the presence of other metals, a single test solution was prepared with the following matrix.

| $Ni^{2+}$ | 10 mg/L |
|---|---|
| $F^-$ | 1.0 mg/L |
| $Zn^{2+}$ | 10 mg/L |
| $Mo^{6+}$ | 10 mg/L |
| $SiO_2$ | 100 mg/L |
| $CO^{2+}$ | 10 mg/L |
| $Pb^{2+}$ | 10 mg/L |
| $NO_2$—N | 50 mg/L |
| $Al^{3+}$ | 10 mg/L |
| $Cd^{2+}$ | 10 mg/L |
| $Cu^{2+}$ | 10 mg/L |
| $Au^{3+}$ | 500 µg/L |
| $Fe^{2+}$ | 100 mg/L |
| $Cr^{6+}$ | 10 mg/L |
| $Ag^+$ | 7 mg/L |
| $Hg^{2+}$ | 1 µg/L |

A second test solution containing only mercury at the same concentration was prepared as the control. The two solutions were digested then analyzed concurrently. There was no interference from the matrix of the test solution at the concentrations listed.

In another test, no interference was observed with a test solution containing the following:

| | |
|---|---|
| Na⁺ | 1000 mg/L |
| K⁺ | 1000 mg/L |
| Mg⁺² | 1000 mg/L |
| Ca⁺² | 400 mg/L |

EXAMPLE 4

A sewage sludge reference standard was obtained from Environmental Resource Associates, Arvada, Colo. This standard is sold is SewageSludg™ Metals, WWS-26, Lot 2612. It has a certified value for mercury of 70.2 mg/Kg (dry) with an advisory range of 44.9 to 100 mg/Kg. The sewage sludge standard does not require drying before analysis. It was analyzed according to the procedure of Examples 1 and 2. The mean results for mercury are equal to 77.7 mg/Kg with a standard deviation of 6.6 mg/Kg.

EXAMPLE 5

Domestic waste water effluent was obtained from the treatment plant of Fort Collins, Colo. The samples contained an average of 0.13 µg/L Hg as determined by analysis according to Examples 1 and 2.

Another sample was then spiked with 2.00 µg Hg. This sample was analyzed according to the present invention. Recovery of the mercury spike was 2.08 µg Hg.

EXAMPLE 6

Samples of industrial waste water were obtained. The waste water did not contain mercury. However, the waste water is a composite of metal finishing, machining, research laboratory and discharges from other operations. The samples were spiked with 3.00 µg Hg and analyzed using the method of Examples 1 and 2.

The mean recovery for the mercury spike was 2.94 µg Hg.

EXAMPLE 7

Replicate analysis of commercial laboratory standards (NIST) was performed according to the procedure described herein. Standards at 1.00 µg/L Hg gave a mean value of 0.96 µg/L Hg with a standard deviation of 0.04 µg/L Hg. Standards at 0.10 µg/L Hg gave a mean value of 0.16 µg/L Hg with a standard deviation of 0.03 µg/L Hg.

What is claimed is:

1. A method for quantitative determination of mercury present in a sample, the method comprising the steps of:
   (a) converting mercury compounds in a sample to elemental mercury;
   (b) removing all elemental mercury from said sample in vapor form by means of vacuum to form a mercury vapor;
   (c) passing the mercury vapor through a column which absorbs and captures all of the mercury vapor by converting the mercury vapor to a mercury halide compound;
   (d) eluting the mercury halide compound from the column; and
   (e) colorimetrically analyzing for the amount of mercury halide compound collected.

2. A method in accordance with claim 1, wherein said sample comprises a liquid.

3. A method in accordance with claim 2, wherein said liquid comprises water.

4. A method in accordance with claim 2, wherein the step of converting mercury compounds in said sample to elemental mercury comprises the steps of acidifying said sample and then digesting said sample in the presence of an oxidizing agent at elevated temperature.

5. A method in accordance with claim 4, further comprising the step of adding a reducing to said sample after said sample has been digested.

6. A method in accordance with claim 5, wherein mercuric ions in said sample are reduced to elemental mercury by addition of stannous sulfate to said sample.

7. A method in accordance with claim 1, wherein said sample comprises solid matter.

8. A method in accordance with claim 1, wherein said column comprises glass beads which have been treated with hypochlorous acid and sodium hypochlorite.

9. A method in accordance with claim 1, further comprising the step of adding an indicator to said eluded mercury halide compound during the step of colorimetrically analyzing for the amount of mercury halide compound.

10. A method in accordance with claim 9, wherein said indicator comprises porphine which forms a mercury:porphine complex with said eluted mercury halide compound.

11. A method in accordance with claim 10, further comprising the steps of (a) measuring absorbance of said eluted mercury halide compound at 412 nm in a spectrophotometer to obtain an absorbance reading at 412 nm, (b) zeroing the absorbance reading at 412 nm, (c) adding a reagent to dissociate said mercury:porphine complex; and (d) measuring absorbance of said eluted mercury halide compound at 412 nm.

12. A method in accordance with claim 11, wherein said reagent for dissociating said mercury:porphine complex comprises L-cycteine.

13. A method in accordance with claim 11, where said reagent for dissociating said mercury:prophine complex is selected from the group consisting of sodium thiosulfate, sodium thioglycolate, and thiourea.

14. A method in accordance with claim 9, wherein said indicator is selected from the group consisting of sulfonated dithizone, porphine derivatives, rodamine 6G, 1,10-penthroline, rose bengal, and antipyrine basic dyes.

15. A method in accordance with claim 1, wherein said column contains an inert particulate material.

16. A method in accordance with claim 15, wherein said particulate material has been treated with hypobromous acid and hypobromite.

17. A method in accordance with claim 1, wherein said column contains silica gel.

18. A method in accordance with claim 1, wherein said column contains liquid bromine.

19. A method in accordance with claim 1, wherein said column contains iodine crystals.

20. A method in accordance with claim 1, wherein mercury present in said sample is less than about 3 parts per billion by weight.

* * * * *